(12) United States Patent
Cherukupally et al.

(10) Patent No.: US 8,969,582 B2
(45) Date of Patent: Mar. 3, 2015

(54) PREPARATION OF FEBUXOSTAT

(75) Inventors: Praveen Cherukupally, Andhra Pradesh (IN); Sreenadha Charyulu Kandala, Andhra Pradesh (IN); Vijay Kumar Adla, Andhra Pradesh (IN); Chandra Sekhar Vempati, Andhra Pradesh (IN)

(73) Assignee: Dr. Reddy's Laboratories Ltd., Hyderabad (IN)

( * ) Notice: Subject to any disclaimer, the term of this patent is extended or adjusted under 35 U.S.C. 154(b) by 54 days.

(21) Appl. No.: 13/642,912

(22) PCT Filed: Apr. 29, 2011

(86) PCT No.: PCT/US2011/034521
§ 371 (c)(1),
(2), (4) Date: Dec. 18, 2012

(87) PCT Pub. No.: WO2011/139886
PCT Pub. Date: Nov. 10, 2011

(65) Prior Publication Data
US 2013/0165662 A1  Jun. 27, 2013

Related U.S. Application Data

(60) Provisional application No. 61/356,117, filed on Jun. 18, 2010, provisional application No. 61/388,640, filed on Oct. 1, 2010.

(30) Foreign Application Priority Data

Apr. 29, 2010 (IN) ............................ 1198/CHE/2010
Jul. 20, 2010 (IN) ............................ 2062/CHI/2010

(51) Int. Cl.
*C07D 277/30* (2006.01)
*C07D 277/56* (2006.01)

(52) U.S. Cl.
CPC ............ *C07D 277/56* (2013.01); *C07D 277/30* (2013.01)
USPC ........................................................ 548/201

(58) Field of Classification Search
CPC ....................................................... C07D 277/30
See application file for complete search history.

(56) References Cited

U.S. PATENT DOCUMENTS

| 4,401,823 | A | * | 8/1983 | Arena ........................... 549/356 |
| 5,614,520 | A | | 3/1997 | Kondo et al. |
| 6,225,474 | B1 | | 5/2001 | Matsumoto et al. |
| 2011/0282069 | A1 | * | 11/2011 | Zhou et al. .................... 548/201 |

FOREIGN PATENT DOCUMENTS

| CN | 101412700 A | 4/2009 |
| CN | 101497589 A | 8/2009 |
| JP | 06345724 A | 12/1994 |
| JP | 10045733 A * | 2/1998 |

OTHER PUBLICATIONS

International Search Report dated, Jan. 18, 2012 for corresponding International Patent Application No. PCT/US2011/034521.

* cited by examiner

*Primary Examiner* — Nyeemah A Grazier
(74) *Attorney, Agent, or Firm* — Pergament Gilman & Cepeda LLP; Milagros A. Cepeda; Edward D. Pergament

(57) ABSTRACT

Processes for preparing febuxostat.

5 Claims, No Drawings

PREPARATION OF FEBUXOSTAT

This application is a National Stage Application under U.S.C. §371 of PCT International Application No. PCT/US2011/034521 filed Apr. 29, 2011, which claims priority to Indian Applications 1198/CHE/2010, filed on Apr. 29, 2010; 2062/CHE/2010, filed on Jul. 20, 2010; and U.S. Provisional Applications 61/356,117, filed on Jun. 18, 2010 and 61/388,640, filed on Oct. 1, 2010; all of which are hereby incorporated herein by reference in their entirety.

INTRODUCTION

Aspects of the present application relate to processes for the preparation of febuxostat. Further aspects relate to an intermediate in the processes. Aspects also relate to processes for the purification of an intermediate in the preparation of febuxostat, and processes for preparing a febuxostat crystalline polymorphic form.

The drug compound having the adopted name "febuxostat" has a chemical name 2-[3-cyano-4-(2-methylpropoxy)phenyl]-4-methylthiazole-5-carboxylic acid, and has the structural formula shown as Formula I.

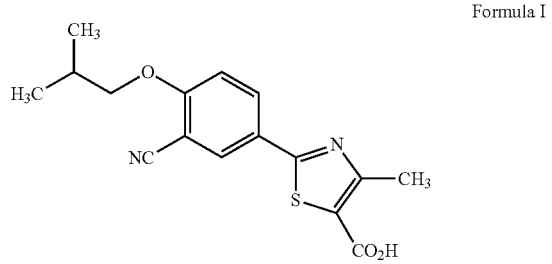 [SMILES: Cc1nc(-c2ccc(OCC(C)C)c(C#N)c2)sc1C(=O)O]

Formula I

Febuxostat is a xanthine oxidase inhibitor and is used for chronic management of hyperuricemia, in patients with gout. Febuxostat is the active ingredient in products sold under the trademark ULORIC®, as 40 and 80 mg tablets.

U.S. Pat. No. 5,614,520 discloses febuxostat and its related compounds. The patent also discloses a process for its preparation, involving hydrolysis of ethyl 2-(3-cyano-4-isobutoxyphenyl)-4-methylthiazole-5-carboxylate of Formula II. The intermediate of Formula II is prepared by reacting 3-cyano-4-isobutoxy benzothiamide with ethyl 2-chloroacetoacetate.

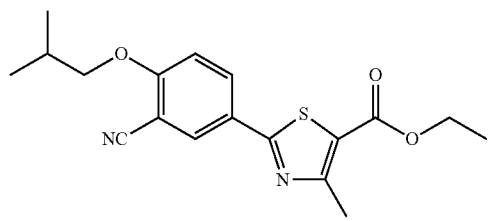

Formula II

Subsequent patents and articles disclose processes for the preparation of febuxostat. The disclosed processes also involve reaction of 3-cyano-4-isobutoxybenzothiamide with ethyl 2-chloroacetoacetate, followed by hydrolysis of the intermediate of Formula II using sodium hydroxide as the base. All of the prior processes disclose the use of ethanol, or its combination with tetrahydrofuran, as the solvent system for the reactions, and purification of the intermediate of Formula II is carried out in ethyl acetate, or by using column chromatography.

The ester intermediate of Formula II serves as the starting material for febuxostat, hence purity of the intermediate of Formula II plays a critical role in determining the purity and yield of febuxostat obtained. Hence, for obtaining febuxostat with high yield and purity it is important to obtain the intermediate of Formula II with high purity.

Various crystalline forms of febuxostat along with their processes for their preparation have been disclosed in various patent applications. Chinese Patent Application Publication No. 101412700 discloses crystalline Form III of febuxostat and a process for its preparation, involving recrystallization of febuxostat in ethyl acetate.

There remains a need for improved processes to prepare febuxostat.

SUMMARY

An aspect of the present application provides processes for the preparation of pure ethyl 2-(3-cyano-4-isobutoxyphenyl)-4-methylthiazole-5-carboxylate of Formula II, comprising reacting 3-cyano-4-isobutoxybenzothiamide of Formula III with ethyl 2-chloroacetoacetate of Formula IV, where Et is an ethyl group, using methanol, a $C_3$ to $C_5$ linear or branched chain alcohol, a hydrocarbon solvent, or water, as a reaction medium.

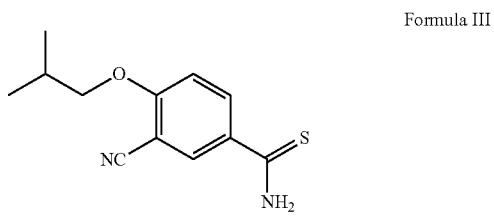

Formula III

Formula IV

An aspect of the present application provides processes for the preparation of febuxostat of Formula I, starting from ethyl 2-(3-cyano-4-isobutoxyphenyl)-4-methylthiazole-5-carboxylate of Formula II, by hydrolysis in the presence of a ketone solvent.

An aspect of the present application provides processes for the preparation of febuxostat of Formula I, starting from ethyl 2-(3-cyano-4-isobutoxyphenyl)-4-methylthiazole-5-carboxylate of Formula II, by hydrolysis using lithium hydroxide as a base.

An aspect of the present application provides processes for the preparation of crystalline Form III of febuxostat.

An aspect of the present application provides pharmaceutical compositions comprising febuxostat prepared according to a process of the present application, together with one or more pharmaceutically acceptable excipients.

DETAILED DESCRIPTION

It has been found that selection of a suitable solvent system for the reaction of 3-cyano-4-isobutoxybenzothiamide with ethyl 2-chloroacetoacetate, to give the ester intermediate of Formula II, and purification of the ester intermediate of Formula II, have a role in determining the purity and yield of febuxostat. The solvent disclosed in the art for this reaction, i.e., ethanol, is not desirable for commercial use, and results in very low yields.

It has also been found that the use of sodium hydroxide, which has been disclosed in the art for hydrolyzing the intermediate of Formula II to give febuxostat, leads to the formation of a high percentage of the amide impurity of Formula Ig in the final product. Therefore, the formation of this impurity can be reduced by choosing an appropriate base for hydrolysis.

After completion of the reaction, the product can be isolated from the reaction mass by complete distillation of the organic layer, or by precipitation of solid after partial distillation and/or by reducing the temperature of the organic layer, followed by decantation, filtration, centrifugation, or any other techniques for separating solids from fluids. It has been observed that the temperatures during the separation can affect the purity of the product obtained. When filtration is conducted at higher temperatures, e.g., in the range of about 40° C. to about 60° C., the purity of the compound of Formula II obtained is high and the percentage of dithiazole ester impurity of Formula Ie in the febuxostat product is low.

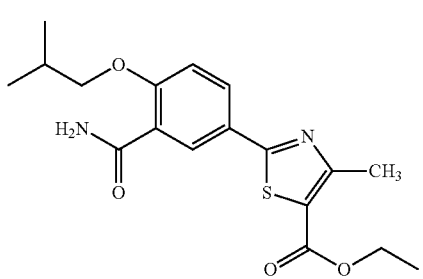

Formula Ig

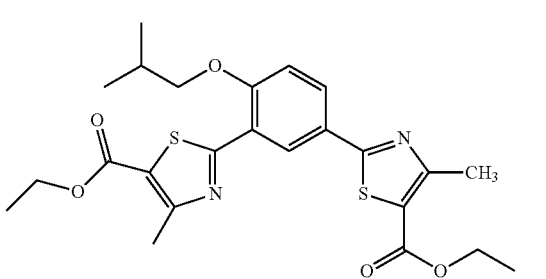

Formula Ie

It has been found that recrystallization in ethyl acetate alone as the solvent leads to low yields of the final product. Hence, there are also provided herein processes for the preparation of crystalline Form III of febuxostat that provide high overall yields.

An aspect of the present application provides processes for the preparation of pure ethyl 2-(3-cyano-4-isobutoxyphenyl)-4-methylthiazole-5-carboxylate of Formula II, comprising reacting 3-cyano-4-isobutoxybenzothiamide of Formula III with ethyl 2-chloroacetoacetate of Formula IV, using methanol, $C_3$ to $C_5$ linear or branched chain alcohols, hydrocarbon solvents, or water as the reaction medium.

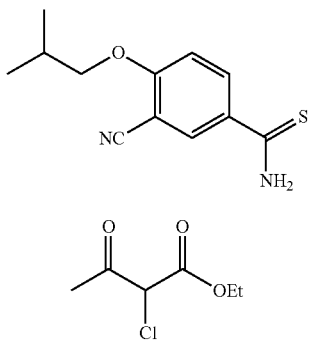

Formula III

Formula IV

Suitable $C_3$ to $C_5$ linear or branched chain alcohols that can be used for the reaction include, but are not limited to isopropyl alcohol, tertiary-butanol, n-butanol, and the like, including mixtures of any two or more thereof. Suitable hydrocarbon solvents that can be used for the reaction include, but are not limited to, toluene, xylene, n-heptane, cyclohexane, and the like, including mixtures of any two or more thereof.

Suitably, the reaction is conducted at the reflux temperature of the solvent used, or it can be conducted at lower temperatures, such as in the range of about 10° C. to about 50° C. The molar ratios of ethyl-2-chloroacetoacetate to 3-cyano-4-isobutoxybenzothiamide of Formula III may range from about 1 to about 3.

In embodiments, the reaction product ethyl 2-(3-cyano-4-isobutoxyphenyl)-4-methylthiazole-5-carboxylate of Formula II can be carried forward to the next stage without isolation.

In embodiments, the present application provides processes for preparing pure ethyl 2-(3-cyano-4-isobutoxyphenyl)-4-methylthiazole-5-carboxylate of Formula II, comprising separating the compound of Formula II by filtering the reaction mass obtained by reacting 3-cyano-4-isobutoxybenzothiamide of Formula III with ethyl 2-chloroacetoacetate of Formula IV, in a hot condition.

The compound of Formula II can be purified using a suitable solvent. Solvents that can be used include, but are not limited to: chloroacetyl chloride; formic acid; ethyl 2-chloroacetoacetate; alcohols such as methanol, ethanol, 2-propanol, 1-butanol, and 2-butanol; dimethylsulfoxide; N,N-dimethylformamide; nitriles such as acetonitrile and propionitrile; ketones; tetrahydrofuran; and the like; including any mixtures of two or more thereof. Purification can be carried out by recrystallization, slurrying, or a combination thereof, in the solvent to obtain a substantially pure compound of Formula II.

For recrystallizing the compound of Formula II in a solvent, the concentration of the compound in the solvent can range from 10-80% or higher. The solution can be prepared at elevated temperature, if desired, to achieve a desired concentration. Any temperatures are acceptable for the dissolution as long as a clear solution is obtained and the stability of the compound is not affected. The recrystallization can use a crude wet compound obtained in a reaction in which the compound of Formula II is formed, or the compound of Formula II can be dried before recrystallizing.

A recrystallization or slurrying process can be repeated multiple times until the product meets the desired specifications for purity. Slurrying of the compound in a solvent can be carried out at temperatures ranging from about 20° C. to about 50° C. The intermediate of Formula II obtained using a process of the present application frequently has a purity at least about 90%, or at least about 95%, as determined using high performance liquid chromatography (HPLC). It can contain less than about 1%, or less than about 0.5%, of individual process-related impurities, such as the compound of Formula Ie.

An aspect of the present application provides processes for preparing febuxostat of Formula I, starting from ethyl 2-(3-cyano-4-isobutoxyphenyl)-4-methyl thiazole-5-carboxylate of Formula II, by hydrolysis in the presence of a ketone solvent. Suitable ketone solvents that can be used for the reaction include, but are not limited to, acetone, ethyl methyl ketone, methyl isobutyl ketone, and the like, including mixtures of any two or more thereof.

Suitable bases that can be used for hydrolysis include, but are not limited to, one or more of: hydroxides of alkali metals, such as lithium hydroxide, sodium hydroxide, potassium hydroxide, and the like; carbonates of alkali metals such as sodium carbonate, potassium carbonate, and the like; and bicarbonates of alkali metals, such as sodium bicarbonate, potassium bicarbonate, and the like. Suitably, aqueous solutions containing about 5% to about 50%, or about 10% to about 20% (w/v) of the base can be used. The amounts of base that can be used in the reaction can vary depending upon the base used. Suitably, the molar ratios of base to the starting material compound of Formula II can range from about 1 to 3:1, or about 1:1. Suitable temperatures for conducting the reaction range from about 30° C. to about 100° C., or from about 40° C. to about 90° C.

In specific embodiments, hydrolysis of ethyl 2-(3-cyano-4-isobutoxyphenyl)-4-methyl thiazole-5-carboxylate of Formula II is carried out using lithium hydroxide as a base. Suitably, aqueous solutions of lithium hydroxide containing about 5% to 50%, or about 10% to 20% (w/v) of the base can be used. Suitably, the molar ratios of lithium hydroxide to the starting material compound of Formula II can range from about 1 to 3:1, or about 1:1. Suitable temperatures for conducting the reaction range from about 30° C. to about 100° C., or from about 40° C. to about 90° C.

After the reaction completion, the reaction mass is taken into water and the pH is made neutral or acidic to form febuxostat. Suitable acids that can be used for adjusting the pH include, but are not limited to, inorganic acids such as sulfuric acid, hydrochloric acid, nitric acid, hydrobromic acid, and the like, including any mixtures of two or more thereof.

Suitable solvents that can be used for extraction of febuxostat from its aqueous solutions include, but are not limited to, water immiscible solvents including: halogenated hydrocarbons, such as dichloromethane, ethylene dichloride, chloroform, and the like; hydrocarbons such as toluene, xylene, n-hexane, n-heptane, cyclohexane, and the like; esters such as ethyl acetate, n-propyl acetate, and the like; ethers such as diethyl ether, diisopropyl ether, methyl tertiary butyl ether, and the like; and any mixtures thereof.

A solid febuxostat product can be recovered from its solutions using techniques such as complete distillation of the solvent, or isolation of the solid in the solution by crystallization, with or without concentration of the solution, followed by decantation, filtration by gravity or by suction, centrifugation, and the like.

The febuxostat that is obtained can be purified by recrystallization, or by slurrying in a suitable solvent. Suitable solvents that can be used for recrystallization or for slurrying of the compound at each stage include, but are not limited to: ketones such as acetone, ethyl methyl ketone, methyl isobutyl ketone, and the like; alcohols such as methanol, ethanol, 1-propanol, isopropyl alcohol, n-butanol, and the like; hydrocarbons such as toluene, xylene, n-hexane, n-heptane, cyclohexane, and the like; halogenated hydrocarbons such as dichloromethane, chloroform, ethylene dichloride, carbon tetrachloride, and the like; and esters such as ethyl acetate, n-propyl acetate, isopropyl acetate, n-butyl acetate, tertiary-butyl acetate, and the like; including any mixtures of two or more thereof, and their mixtures with water in various proportions.

The wet solid that is obtained can be optionally be dried. Drying can be suitably carried out using a tray dryer, vacuum oven, air oven, fluidized bed dryer, spin flash dryer, flash dryer, and the like. The drying can be carried out at temperatures about 35° C. to about 70° C., for any desired time periods to achieve a desired purity, times from about 1 to 20 hours, or longer, frequently being suitable.

Febuxostat obtained according to a process of the present application is substantially pure. By "substantially pure" it is meant that febuxostat prepared in accordance with a process of the present application has a purity at least about 99%, or at least about 99.5%. It contains less than about 0.5%, or less than about 0.15%, by weight of any of the process-related impurities. More particularly, it contains less than about 0.5%, or less than about 0.1%, of each of the following potential process-related impurities:

(1) 2-(3-Cyano-4-isobutoxy-phenyl)-4-methyl-thiazole-5-carboxylic acid isopropyl ester of Formula Ia;

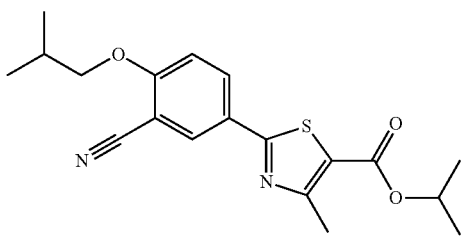

Formula Ia (2) 2-Isobutoxy-5-(4-methyl-thiazol-2-yl)-benzonitrile of Formula Ib;

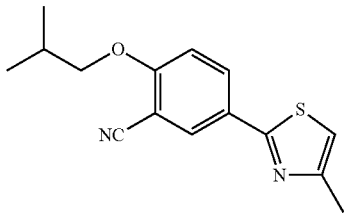

Formula Ib (3) 2-[3-Cyano-4-(2-methyl-allyloxy)-phenyl]-4-methyl-thiazole-5-carboxylic acid ethyl ester of Formula Ic;

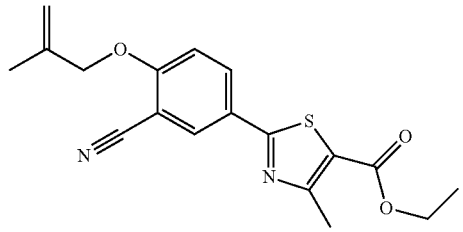

Formula Ic (4) 2-[3-Cyano-4-(2-methyl-allyloxy)-phenyl]-4-methyl-thiazole-5-carboxylic acid of Formula Id;

Formula Id

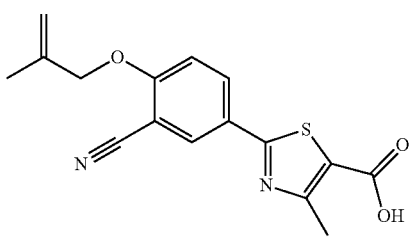

(5) diethyl 2,2'-(4-isobutoxy-1,3-phenylene) bis(4-methylthiazole-5-carboxylate) of Formula Ie;

Formula Ie

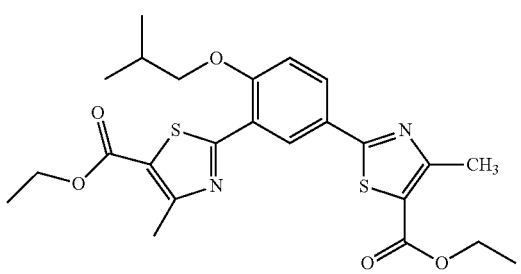

(6) ethyl 2-(3-cyano-4-(isobutylamino)phenyl)-4-methylthiazole-5-carboxylate of Formula If;

Formula If

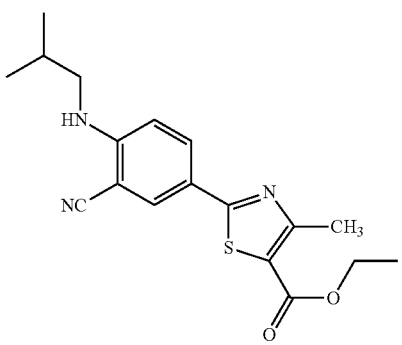

(7) diethyl 2,2'-(4-isobutoxy-1,3-phenylene) bis(4-methylthiazole-5-carboxylic acid) of Formula Ih; and Formula Ih

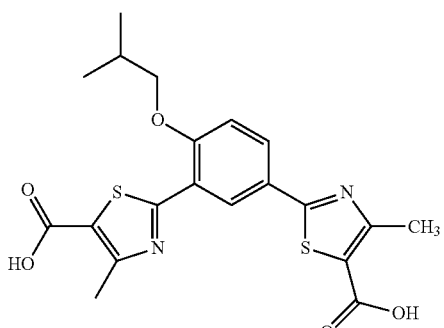

(8) the compound of Formula II.

Formula II

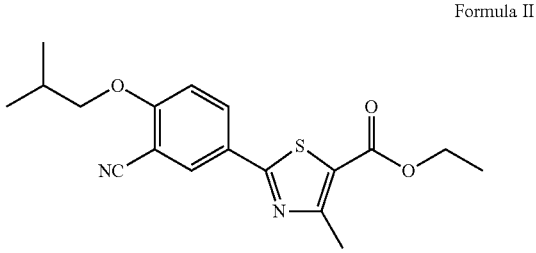 [SMILES: CCOC(=O)c1sc(-c2ccc(OCC(C)C)c(C#N)c2)nc1C]

Febuxostat obtained using a process of the present application contains less than about 5000 ppm, or less than about 3000 ppm, or less than about 1000 ppm, by weight of individual residual organic solvents.

An aspect of the present application provides processes for the preparation of crystalline Form III of febuxostat, involving crystallization of febuxostat in a system comprising an ester and a hydrocarbon.

Suitable esters include, but are not limited to, ethyl acetate, n-propyl acetate, isopropyl acetate, n-butyl acetate, tertiary-butyl acetate, and the like, and suitable hydrocarbons include, but are not limited to, toluene, xylene, n-hexane, n-heptane, cyclohexane, and the like.

Suitably, recrystallization is carried out using a solvent-antisolvent technique, by dissolving febuxostat in the ester and adding the anti-solvent hydrocarbon to it. Suitably, the ester for dissolution may be present in amounts about 0.5 to about 50 volumes (mL per gram of febuxostat), or from about 0.5 to about 20 volumes. Dissolution may be carried out at temperatures ranging from about 25° C. to about 100° C., or from about 25° C. to about 60° C., to facilitate complete dissolution of febuxostat. A higher initial volume of ester may be taken for dissolution, and then the initial volume reduced to a desired volume by evaporation, such as at elevated temperatures and/or reduced pressures.

The solution of fubuxostat may be combined with an anti-solvent hydrocarbon slowly, such as over about 30 minutes to about 4 hours. The anti-solvent may be used in amounts about 5 to about 50 volumes (mL of antisolvent per gram of febuxostat) to produce a suspension. The ratio of the ester to the anti-solvent affects precipitation of the product, and should be experimentally determined for particular solution concentrations, by techniques that are known in the art. Optionally, the suspension obtained after combination with the anti-solvent is cooled to a lower temperature, such as about −10° C. to about 25° C., to enhance precipitation.

The methods by which the solid material is recovered from the final mixture, with or without cooling below the operating temperature, may be any techniques, such as, for example, decantation, filtration by gravity or suction, centrifugation, and the like. If desired, the crystals may be washed with a solvent after recovery. The wet cake obtained can optionally be dried. Drying can be suitably carried out using a tray dryer, vacuum oven, air oven, fluidized bed dryer, spin flash dryer, flash dryer, and the like. The drying can be carried out at temperatures about 35° C. to about 70° C., for any desired time periods to achieve a desired purity, times from about 1 to 20 hours, or longer, frequently being suitable.

An aspect of the application provides pharmaceutical compositions comprising febuxostat obtained using a process of the present application, together with one or more pharmaceutically acceptable excipients.

The pharmaceutical compositions comprising febuxostat and its combination with pharmaceutically acceptable excipients of this application may be formulated as solid oral dosage forms such as, but not limited to: powders, granules, pellets, tablets, and capsules; liquid oral dosage forms such as but not limited to syrups, suspensions, dispersions, and emulsions; and injectable preparations such as but not limited to solutions, dispersions, and freeze-dried compositions. Formulations may be in the form of immediate release, delayed release, or modified release. Further, immediate release compositions may be conventional, dispersible, chewable, mouth dissolving, or flash melt preparations, and modified release compositions may comprise hydrophilic or hydrophobic, or combinations of hydrophilic and hydrophobic, release rate controlling substances to form matrix or reservoir, or combination of matrix and reservoir, systems. The compositions may be prepared using any of direct blending, dry granulation or wet granulation, or extrusion and spheronization techniques. Compositions may be presented as uncoated, film coated, sugar coated, powder coated, enteric coated, or modified release coated.

Pharmaceutically acceptable excipients that are useful in the present application include, but are not limited to: diluents such as starch, pregelatinized starch, lactose, powdered cellulose, microcrystalline cellulose, dicalcium phosphate, tricalcium phosphate, mannitol, sorbitol, sugar, and the like; binders such as acacia, guar gum, tragacanth, gelatin, polyvinylpyrrolidones, hydroxypropyl celluloses, hydroxypropyl methylcelluloses, pregelatinized starches, and the like; disintegrants such as starches, sodium starch glycolate, pregelatinized starches, crospovidones, croscarmellose sodium, colloidal silicon dioxide, and the like; lubricants such as stearic acid, magnesium stearate, zinc stearate, and the like; glidants such as colloidal silicon dioxide and the like; solubility or wetting enhancers such as anionic, cationic, and neutral surfactants; complex forming agents such as various grades of cyclodextrins and resins; release rate controlling agents such as hydroxypropyl celluloses, hydroxymethyl celluloses, hydroxypropyl methylcelluloses, ethylcelluloses, methylcelluloses, various grades of methyl methacrylates, waxes, and the like. Other pharmaceutically acceptable excipients that useful include, but are not limited to, film formers, plasticizers, colorants, flavoring agents, sweeteners, viscosity enhancers, preservatives, antioxidants, and the like.

In the compositions of present application febuxostat is a useful active ingredient in the range of about 20-30 mg, or 30-80 mg, per dosage unit.

Definitions

The following definitions are used in connection with the present application unless the context indicates otherwise. An "ester" is an organic compound containing a carboxyl group —(C=O)—O— bonded to two other carbon atoms, including but not limited to ethyl acetate, n-propyl acetate, n-butyl acetate, isobutyl acetate, t-butyl acetate, and the like.

A "ketone" solvent is an organic compound containing a carbonyl group —(C=O)— bonded to two other carbon atoms, including but are not limited to acetone, ethyl methyl ketone, diethyl ketone, methyl isobutyl ketone, $C_{3-6}$ ketones, and the like.

An "aromatic hydrocarbon" is a liquid, unsaturated, cyclic, hydrocarbon containing one or more rings, including at least one 6-carbon ring containing three double bonds. Examples include, but are not limited to, benzene, toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$ aromatic hydrocarbons, and mixtures thereof.

A "hydrocarbon" is a liquid, saturated hydrocarbon, which may be linear, branched, or cyclic. Examples include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$ aliphatic hydrocarbons, and mixtures thereof.

Polymorphs are different solids sharing the same molecular formula, yet having distinct physical properties when compared to other polymorphic forms having the same formula. Various polymorphs may be distinguished using analytical techniques such as X-ray diffraction and thermal analysis.

The term "reacting" is intended to represent bringing the chemical reactants together, under conditions that cause the chemical reaction indicated to take place.

Certain specific aspects and embodiments of the present application will be explained in more detail with reference to the following examples, which are provided only for purposes of illustration and should not be construed as limiting the scope of the application in any manner.

EXAMPLE 1

Preparation of Ethyl 2-(3-Cyano-4-Isobutoxyphenyl)-4-Methylthiazole-5-Carboxylate (Formula II)

Isopropyl alcohol (50 mL) was placed into a round bottom flask and 3-cyano-4-isobutoxybenzothioamide (5.0 g) was added, followed by addition of ethyl-2-chloroacetoacetate (4.25 g). The mixture was heated to reflux and maintained until reaction completion. After the reaction was completed, the mass was cooled to about 25° C. and maintained for about 30 minutes. The mass was then filtered and the solid was washed with isopropyl alcohol (10 mL). The wet solid was dried at about 75° C. to a constant weight to yield 6.2 g of the title compound. Purity by HPLC: 98.31%.

EXAMPLE 2

Preparation of Ethyl 2-(3-Cyano-4-Isobutoxyphenyl)-4-Methylthiazole-5-Carboxylate (Formula II)

Toluene (50 mL) was placed into a round bottom flask and 3-cyano-4-isobutoxybenzothioamide (5.0 g) was added, followed by addition of ethyl-2-chloroacetoacetate (4.25 g). The mixture was heated to reflux and maintained until reaction completion. After the reaction was completed, the mass was cooled to about 25° C. and maintained at that temperature for about 20 minutes. The reaction mass was then filtered and the solid was washed with toluene (10 mL). The wet solid was dried at about 75° C. to a constant weight to yield 4.0 g of the title compound. Purity by HPLC: 99.41%.

EXAMPLE 3

Preparation of Ethyl 2-(3-Cyano-4-Isobutoxyphenyl)-4-Methylthiazole-5-Carboxylate (Formula II)

Water (30 mL) was placed into a round bottom flask and 3-cyano-4-isobutoxybenzothioamide (3.0 g) was added, followed by addition of ethyl-2-chloroacetoacetate (2.52 g). The mixture was heated to reflux and maintained until reaction completion. After the reaction was completed, the mass was cooled to about 25° C. and maintained for about 20 minutes. The mass was then filtered. The wet solid was dried at about 60° C. to a constant weight to yield 4.0 g of the title compound. Purity by HPLC: 95.74%.

EXAMPLE 4

Preparation of Ethyl 2-(3-Cyano-4-Isobutoxyphenyl)-4-Methylthiazole-5-Carboxylate (Formula II)

Methanol (50 mL) was placed into a round bottom flask and 3-cyano-4-isobutoxy benzothioamide (5.0 g) was added, followed by addition of ethyl-2-chloroacetoacetate (4.25 g). The mixture was heated to reflux and maintained until reaction completion. After the reaction was completed, the mass was cooled to about 25° C. and maintained for about 30 minutes. The mass was then filtered and washed with methanol. The wet solid was dried at about 70° C. to a constant weight to yield 5.0 g of the title compound. Purity by HPLC: 84.9%.

EXAMPLE 5

Purification of Ethyl 2-(3-Cyano-4-Isobutoxyphenyl)-4-Methylthiazole-5-Carboxylate (Formula II)

Crude ethyl 2-(3-cyano-4-isobutoxyphenyl)-4-methylthiazole-5-carboxylate (20.0 g), was placed into a round bottom flask and chloroacetyl chloride (60 mL) was added. The mixture was heated to about 75-85° C. and maintained for 1 hour. The mixture was cooled to about 0-5° C. and isopropyl alcohol (160 mL) was added at the same temperature. The mixture then maintained at 25-35° C. for about 1 to 2 hours and filtered. The collected solid was washed with isopropyl alcohol (80 mL). The wet solid was dried at about 60-70° C. to a constant weight to yield 24.3 g of the title compound. Purity by HPLC: 98.8%.

EXAMPLE 6

Preparation of Ethyl 2-(3-Cyano-4-Isobutoxyphenyl)-4-Methylthiazole-5-Carboxylate (Formula II)

3-Cyano-4-isobutoxybenzothioamide (100.0 g), ethyl-2-chloroacetoacetate (91.29 g), and isopropyl alcohol (700 mL) were placed into a round bottom flask and stirred for about 30 minutes. The mixture was heated to reflux and maintained at that temperature until reaction completion. After the reaction was complete, the mass was cooled to about 55° C. and maintained for about 30 minutes. The mass was filtered at the same temperature and the solid was washed with hot isopropyl alcohol (400 mL). The wet solid was dried at about 60° C. to a constant weight to yield 156.4 g of the title compound. Purity by HPLC: 98.8%.

EXAMPLE 7

Preparation of Febuxostat

Ethyl 2-(3-cyano-4-isobutoxyphenyl)-4-methylthiazole-5-carboxylate (3.0 g), acetone (30 mL), and 1 N sodium hydroxide solution (12 mL) were placed into a round bottom flask and heated to reflux. The mixture was maintained under reflux until reaction completion. After the reaction was completed, the mass was cooled to about 25° C. and the pH was adjusted to about 1 to 2 with hydrochloric acid (1.5 mL). The mass was extracted into ethyl acetate (40 mL). The ethyl acetate layer was washed with water (30 mL). The ethyl acetate layer was distilled completely under vacuum below 60° C. Acetone (30 mL) was added to the residue and the mixture was heated to reflux and maintained for about 30 minutes. The mass was then cooled to about 25° C., maintained for about 60 minutes, filtered under vacuum and the solid was washed with acetone (3 mL). The wet solid was dried at about 60° C. to a constant weight to yield 1.0 g of the title compound. Purity by HPLC: 99.5%.

EXAMPLE 8

Preparation of Febuxostat

Ethyl 2-(3-cyano-4-isobutoxyphenyl)-4-methylthiazole-5-carboxylate (50.0 g), acetone (500 mL), water (200 mL), and sodium hydroxide (6.96 g) were placed into a round bottom flask and heated to reflux. The mixture was maintained under reflux until reaction completion. After the reaction was completed, the mass was cooled to about 25° C., water (500 mL) and ethyl acetate (500 mL) were added, and the pH was adjusted to about 1 to 2 with hydrochloric acid (10.3 mL). The organic layer was separated and the aqueous layer was extracted into ethyl acetate (250 mL). The ethyl acetate layer was washed with water (300 mL). The ethyl acetate layer was distilled completely under vacuum below 60° C. The residue was dried at about 60° C. under vacuum to a constant weight to yield 1.0 g of the title compound. Purity by HPLC: 98.9%.

EXAMPLE 9

Preparation of Febuxostat

Ethyl 2-(3-cyano-4-isobutoxyphenyl)-4-methylthiazole-5-carboxylate (8.0 Kg), acetone (80 L), lithium hydroxide monohydrate (1.2 Kg), and water (12 L) were mixed and heated to reflux. The mixture was maintained under reflux until reaction completion. After the reaction was complete, the mass was cooled to about 25° C., ethyl acetate (120 L) was added, and pH was adjusted to about 1 to 2 with hydrochloric acid (3.2 L). The organic layer was separated and the aqueous layer was extracted with ethyl acetate (80 L). The combined organic material was washed with water (3×80 L), and treated with activated carbon at about 50° C. The combined organic material was filtered, and the filtrate was evaporated completely under vacuum below 45° C. Acetonitrile (16 L) was added to the residue and the solvent was distilled. Acetonitrile (80 L) was added to the residue and the mixture was heated to about 65° C. and maintained for about 1 hour. The mass was cooled to about 30° C. and maintained for about 1 hour. The formed solid was filtered and washed with acetonitrile (32 L). The wet solid was dried at about 60° C. to a constant weight to yield 5.2 Kg of the title compound. Purity by HPLC: 99.9%.

EXAMPLE 10

Preparation of Crystalline Febuxostat Form III

Febuxostat (3.0 Kg), obtained using a process similar to that described in Example 9, and ethyl acetate (73 L) were mixed and the mass was heated to 75-80° C. and maintained for about 30 minutes. The mass was allowed to cool to about 40° C., n-heptane (113 L) was added, and the mass was then allowed to cool to about 30° C. and maintained for 1 hour. The formed solid was collected by filtration and dried at about 60° C. to a constant weight to yield 2.0 Kg of the title compound. Purity by HPLC: 99.9%.

The invention claimed is:

1. A process for preparing febuxostat, comprising hydrolyzing ethyl 2-(3-cyano-4-isobutoxyphenyl)-4-methylthiazole-5-carboxylate in the presence of a ketone solvent.

2. The process of claim 1, wherein a ketone solvent comprises acetone, ethyl methyl ketone, or methyl isobutyl ketone.

3. The process of claim 1, wherein a ketone solvent is acetone.

4. The process of claim 1, wherein hydrolyzing comprises reacting with lithium hydroxide.

5. The process of claim 4, wherein lithium hydroxide is used in the form of an aqueous solution.

* * * * *